(12) United States Patent
Weaver et al.

(10) Patent No.: US 6,713,641 B2
(45) Date of Patent: Mar. 30, 2004

(54) REACTIVE ANTHRAQUINONE COLORANT COMPOUNDS AND POLYMERIC MATERIALS REACTED THEREWITH

(75) Inventors: Max Allen Weaver, Kingsport, TN (US); Gerry Foust Rhodes, Piney Flats, TN (US); Jason Clay Pearson, Kingsport, TN (US); Sara Stanley Wells, Kingsport, TN (US); Michael John Cyr, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 204 days.

(21) Appl. No.: 10/046,679

(22) Filed: Oct. 19, 2001

(65) Prior Publication Data

US 2003/0125505 A1 Jul. 3, 2003

(51) Int. Cl.[7] .................. C09B 62/004; C09B 62/465
(52) U.S. Cl. .................. 552/254; 552/238; 552/74; 552/78; 552/79; 552/90; 552/96; 552/100; 552/104; 552/178; 552/179; 552/182; 430/517; 430/521; 430/533; 528/271; 528/272; 528/274; 528/288; 528/291; 8/489; 8/512
(58) Field of Search .................. 522/74, 78, 79, 522/90, 96, 100, 104, 107, 178, 179, 182, 238, 254; 528/271, 272, 274, 288, 291; 8/489, 512; 430/517, 512, 533

(56) References Cited

U.S. PATENT DOCUMENTS

| | | |
|---|---|---|
| 3,413,257 A | 11/1968 | Bowman et al. |
| 3,488,195 A | 1/1970 | Hunter |
| 3,849,139 A | 11/1974 | Hibino et al. |
| 3,918,976 A | 11/1975 | Arai et al. |
| 3,933,502 A | 1/1976 | Arai et al. |
| 4,025,492 A | 5/1977 | Binsack et al. |
| 4,115,056 A | 9/1978 | Koller et al. |
| 4,136,089 A | 1/1979 | Bier et al. |
| 4,176,224 A | 11/1979 | Bier et al. |
| 4,208,527 A | 6/1980 | Horlbeck et al. |
| 4,238,593 A | 12/1980 | Duh |
| 4,943,617 A | 7/1990 | Etzbach et al. |
| 5,055,602 A | 10/1991 | Melpolder |
| 5,109,097 A | 4/1992 | Klun et al. |
| 5,362,812 A | 11/1994 | Holmes et al. |
| 5,367,039 A | 11/1994 | Yabuuchi et al. |
| 5,372,864 A | 12/1994 | Weaver et al. |
| 5,578,419 A | 11/1996 | Itoh et al. |
| 5,744,294 A | 4/1998 | Dickerson et al. |

FOREIGN PATENT DOCUMENTS

| | | |
|---|---|---|
| EP | 0 322 808 | 7/1989 |
| EP | 0 396 376 | 11/1990 |
| JP | 55-038825 | 3/1980 |
| JP | 62-061065 | 12/1987 |
| WO | WO 92/13921 | 8/1992 |
| WO | WO 96/01283 | 1/1996 |
| WO | WO 97/48744 | 12/1997 |

OTHER PUBLICATIONS

Asquith et al, "Self Coloured Polymers Based on Anthraquinone Residues", Journal of the Society of Dyers and Colourists (J.S.D.C.), Apr. 1977, pp. 114–125.
R. E. Wilfong, Journal of Polymer Science, vol. 54, pp. 385–410, 1961.
John Wiley & Sons, Chemistry and Technology of UV and EB Formulations for Coatings, Inks, and Paints, vol. 11: Prepolymers and Reactive Diluents, G. Webster, London, 1997, pp. 35–250.

*Primary Examiner*—James J. Seidleck
*Assistant Examiner*—Sanza L. McClendon
(74) *Attorney, Agent, or Firm*—Michael J. Blake; Bernard J. Graves, Jr.

(57) ABSTRACT

Disclosed are blue, diol anthraquinone blue colorant compounds having excellent thermal stability and which can be reacted into or copolymerized with polyester thus providing a blue-colored polyesters useful for manufacturing a variety of shaped articles such as photographic film base, particularly roentgenographic (X-ray) film. Also disclosed are blue anthraquinone colorant compounds which contain two ethylenically-unsaturated (vinyl), photopolymerizable radicals which may be derived from the aforesaid diol anthraquinone compounds. The anthraquinone colorant compounds containing two ethylenically-unsaturated may be reacted into or copolymerized (or cured) with ethylenically-unsaturated monomers to produce colored vinyl polymers.

21 Claims, No Drawings

REACTIVE ANTHRAQUINONE COLORANT COMPOUNDS AND POLYMERIC MATERIALS REACTED THEREWITH

FIELD OF THE INVENTION

The present invention pertains to certain novel blue, diol anthra-quinone blue colorant compounds having excellent thermal stability and which can be reacted into or copolymerized with polyester thus providing a blue-colored polyesters useful for manufacturing a variety of shaped articles such as photographic film base, particularly roentgenographic (X-ray) film. This invention also pertains to certain novel blue anthraquinone colorant compounds which contain two ethylenically-unsaturated (vinyl), photopolymerizable radicals which may be derived from the aforesaid diol anthraquinone compounds. The anthraquinone colorant compounds containing two ethylenically-unsaturated may be reacted into or copolymerized (or cured) with ethylenically-unsaturated monomers to produce colored vinyl polymers.

BACKGROUND

X-ray film typically contains a blue colorant to facilitate the perception of the photographic image. The blue-tinted film bases serve to prevent the disadvantages with roentgenographic materials in which a photographic emulsion is provided on both surfaces of the film support and wherein a filter desensitization action results in that the photographic images have a yellow fog or haze, thus interfering with the image definition. It is desirable that the blue colorant (or toner) has a minimum light absorbance in the short wavelength region in the visible light absorption spectrum, particularly in the 400–450 nm range so that no additional yellow color be introduced into the film. Blue colorants for X-ray film also should be thermally stable, soluble in the polyester, resistant to sublimation and stable to conditions that may be encountered during storage, such as high humidity. The colorant must have no adverse effect upon the gelatin-silver halide emulsion coated onto the blue-colored film base.

It is known to use various blue anthraquinone colorant compounds to impart the necessary blue hue to the polyester, e.g., poly(ethylene terephthalate), particularly 1,4-bis(2',6'-dialkylanilino)anthraquinone compounds as well as blue anthraquinone dyes containing hydroxy and arylamino groups. See, for example, the anthraquinone compounds disclosed in U.S. Pat. Nos. 3,488,195; 3,849,139; 3,918,976; and 3,933,502. In the prior art, the tinted poly(ethylene terephtalate) (PET) is colored by the so-called dope dyeing method which involves drying PET pellets, mixing the colorant with the PET, followed by heating the mixture, extruding, stretching and heat-treating the melt and forming it into film. Without the drying step, the starting polyester will undergo hydrolysis upon heat-melting, which results in polymer degradation which produces film having inferior and inadequate properties. The colorant compounds must possess sufficient heat stability to withstand molding or extrusion temperatures as high as 270° C.–300° C. For color control, it also is desirable to prepare a masterbatch by blending PET pellets or chips with the colorant using a dry blending method followed by kneading and melt extruding to produce a colored concentrate composition, e.g., a colorant concentration of about 1%. The masterbatch then is mixed with additional uncolored PET pellets and melt blended and extruded to produce a polyester, typically in the form of pellets, having a total colorant content of about 100–400 parts per million be weight (ppmw).

In the coloring process described above, it is necessary, of course, to use a colorant that can be readily dispersed and dissolved in a polyester to achieve uniformity during the extrusion process, since the film support must have a high degree of transparency and be completely free of optical imperfections. Problems associated with the above-described process include sublimation and volatility problems encountered during the extruding and heat stretching steps, resulting in loss of colorant and contamination of equipment and surrounding areas. Also, when a masterbatch is required to achieve uniformity, the step added by formation of the masterbatch increases the costs to the overall coloration process. In either case, the required handling of dry powder colorant is hazardous and results in unavoidable contamination problems. Furthermore, uniformity problems are encountered unless melt blending and extruding times are extended to ensure adequate mixing and solubilization of the colorant.

It also is known to color polyesters such as PET by adding the colorants during the polyester preparation step, e.g., as described in U.S. Pat. No. 3,488,195, column 2, lines 43–45. Such addition of a colorant during polyester synthesis occasions longer periods of time at high temperature causing more pronounced problems of colorant volatility resulting in loss of dye by sublimation. Also, colorants having higher thermal stability are needed. Furthermore, the blue anthraquinone dyes having aromatic hydroxy groups and arylamino groups change shades usually toward green under polyester manufacturing conditions, presumably as a result of metalization, rendering the resulting colored polyester unsuitable for use in manufacturing X-ray film.

U.S. Pat. No. 5,372,864 discloses certain 1,4-bis(2',6'-dialkylanilino)-anthraquinone colorant compounds substituted with sulfonamide groups which contain polyester-reactive groups and which have been copolymerized into polyesters at low levels. Efforts to utilize the disclosed reddish-blue colorants of Formula I U.S. Pat. No. 5,372,864 to color polyesters by copolymerization during polyester manufacture have provided colored polyesters wherein the blue colorant is too hypsochromic, i.e., too red, in color to be suitable as toners or colorants for X-ray film and require the addition of second colorant compound such as a cyan phthalocyanine, e.g., as described in U.S. Pat. No. 5,744,294. WO 92/13921 discloses various functionalized chromophores, including anthraquinone colorant compounds and the copolymerization of the functionalized chromophores into polyesters to prepare color concentrates. The color concentrates are used as colorants for a variety of thermoplastic polymeric materials including polyesters. However, WO 92/13921 does not describe any anthraquinone colorant compound which is suitable for the tinting or coloration of X-ray film. Similarly, Solvent Blue 45 having the formula:

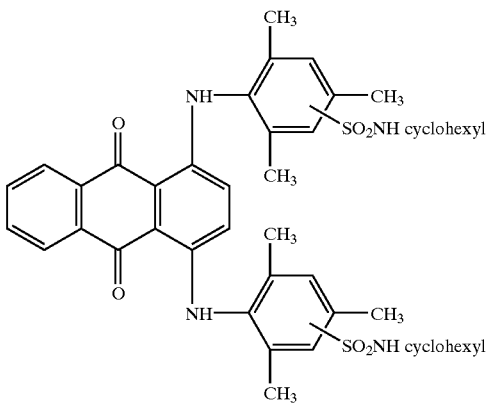

has been proposed as a colorant for X-ray film. However, Solvent Blue 45 also is too red and greener blue dyes are recommended for shading to produce a more neutral blue colorant system. See, for example, Japanese patent documents JP 55-038825 A2 and JP 62-061065 B4. The addition of a second dye, of course, greatly contributes to the difficulty of color control.

As stated above, the present invention also pertains to certain novel blue anthraquinone colorant compounds which contain at least two ethylenically-unsaturated, photopolymerizable radicals which may be reacted into or copolymerized (or cured) with ethylenically-unsaturated monomers to produce colored vinyl polymers. It is known (J.S.D.C., April 1977, pp 114–125) to produce colored polymeric materials by combining a reactive polymer such as terepolymers having epoxy groups or polyacryloyl chloride with anthraquinone dyes containing nucleophilic reactive groups such as amino or hydroxy groups; to graft acryloylaminoanthraquinone dyes to the backbone of vinyl or divinyl polymers; and to polymerize anthraquinone dyes containing certain olefinic groups to produce polymeric dyes/pigments. U.S. Pat. No. 4,115,056 describes the preparation of blue, substituted 1,4-diaminoanthraquinone dyes containing one acryloyloxy group and the use of the dyes in coloring various fibers, especially polyamide fibers. U.S. Pat. No. 4,943,617 discloses liquid crystalline copolymers containing certain blue, substituted 1,5-diamino-4,8-dihydroxy-anthraquinone dyes containing an olefinic group copolymerized therein to provide liquid crystal copolymers having high dichromism. U.S. Pat. No. 5,055,602 describes the preparation of certain substituted 1,4-diamino-anthraquinone dyes containing polymerizable acryloyl and methacryloyl groups and their use in coloring polyacrylate contact lens materials by copolymerizing.

U.S. Pat. No. 5,362,812 discloses the conversion of a variety of dye classes, including anthraquinones, into polymeric dyes by (a) polymerizing 2-alkenylazlactones and reacting the polymer with dyes containing nucleophilic groups and by (b) reacting a nucleophilic dye with an alkenyl-azlactones and then polymerizing the free radically-polymerizable dyes thus produced. The polymeric dyes are reported to be useful for photoresist systems and for color-proofing. U.S. Pat. No. 5,367,039 discloses a process for preparing colored vinyl polymers suitable for inks, paints, toners and the like by emulsion polymerization of a vinyl monomer with reactive anthraquinone dyes prepared by functionalizing certain anthraquinone dyes with methacryloyl groups.

U.S. Pat. No. 5,055,602 discloses in Example Ii, column 7, the vinyl functionalized anthraquinone colorants having the structure:

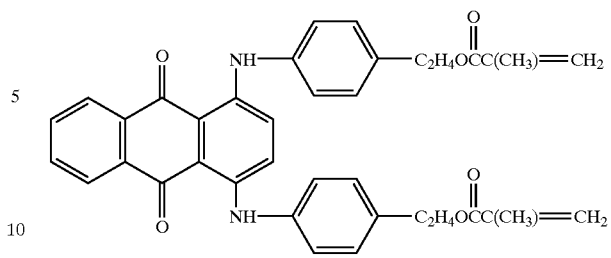

This anthraquinone colorant compound exhibits considerable light absorption at wavelengths of from 400–450 nm which gives the colorant compound a green appearance, thus rendering it unsuitable for use as a colorant for typical three component colorant blends useful for producing the entire range of shades desired. The preparation of a variety of dyes, including some anthraquinones, which contain photopolymerizable groups and their use for color filters suitable for use in liquid crystal television sets, color copying machines, photosensitive resist resin compositions, and the like are described in U.S. Pat. No. 5,578,419.

SUMMARY OF THE INVENTION

The present invention is comprised of a plurality of embodiments the first of which is a novel class of anthraquinone colorant compounds having the formula

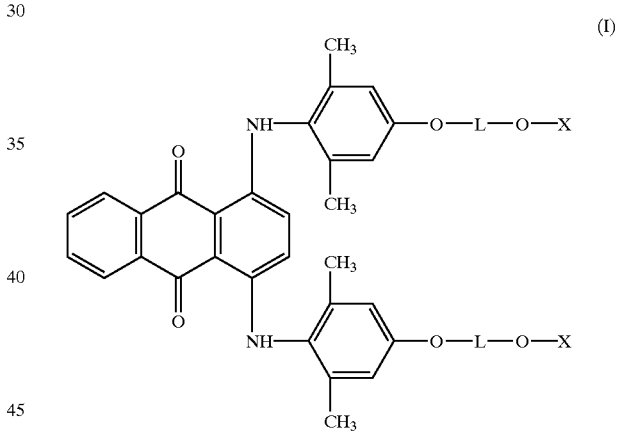

(I)

wherein L is a linking group selected from $C_2$–$C_8$-alkylene, $-(-CH_2CH_2O-)_n-CH_2CH_2-$ and $-CH_2-$cyclohexylene4—$CH_2$—, wherein n is 1 or 2; and X is hydrogen or the residue of an acylating agent. A second embodiment of our invention is a molding or extrusion grade polyester having reacted therewith or copolymerized therein at least one of the compounds of formula (I). The colorant compounds having formula (I) are thermally stable and do not volatilize under polyester manufacturing conditions and do not sublime, exude or migrate from the polyester during the film extrusion process or after the film is formed. The colorant compounds provide strong absorbance of light at wavelengths of from about 600 nm to about 650 nm and a minimum of absorbance in the 400 nm to about 550 nm range thus providing a pure blue color suitable for use as an X-ray film toner. A third embodiment of the present invention pertains to an X-ray film element comprising a film base comprised of a polyester having reacted therewith or copolymerized therein at least one of the compounds of formula (I).

A fourth embodiment of the present invention pertains to anthraquinone colorant compounds having the formula:

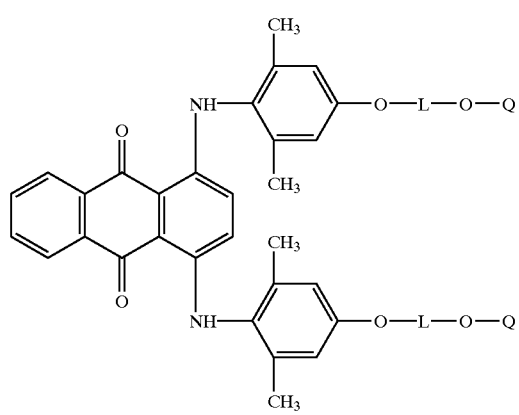

(II)

wherein L is defined above and Q is a photopolymerizable group selected from the radicals having the formulae:

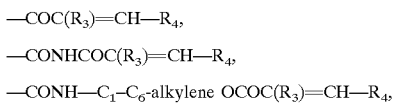

—COC(R$_3$)=CH—R$_4$,    1

—CONHCOC(R$_3$)=CH—R$_4$,    2

—CONH—C$_1$-C$_6$-alkylene OCOC(R$_3$)=CH—R$_4$,    3

4

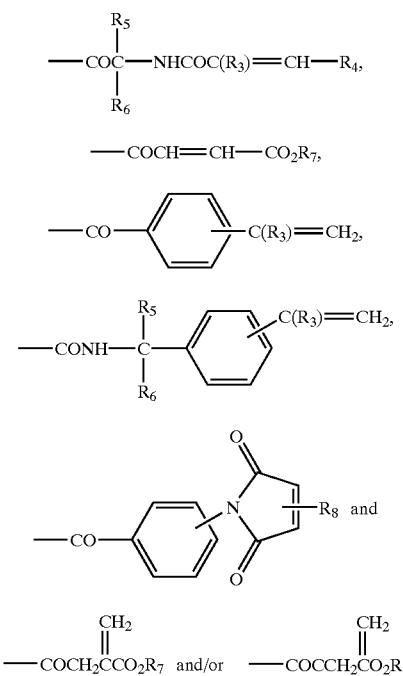

—COC(R$_5$)(R$_6$)—NHCOC(R$_3$)=CH—R$_4$,

—COCH=CH—CO$_2$R$_7$,    5

6

7

—CONH—C(R$_5$)(R$_6$)—C$_6$H$_4$—C(R$_3$)=CH$_2$,

8

—COCH$_2$CCO$_2$R$_7$ and/or —COCCH$_2$CO$_2$R$_7$    9 wherein

R$_3$ is selected from hydrogen or C$_1$–C$_6$-alkyl;

R$_4$ is selected from hydrogen; C$_1$–C$_6$-alkyl; phenyl; phenyl substituted with one or more groups selected from C$_1$–C$_6$-alkyl, C$_1$–C$_6$-alkoxy, —N(C$_1$–C$_6$-alkyl)$_2$, nitro, cyano, C$_2$–C$_6$-alkoxycarbonyl, C$_2$–C$_6$-alkanoyloxy and halogen; 1- and 2-naphthyl; 1- and 2-naphthyl substituted with C$_1$–C$_6$-alkyl or C$_1$–C$_6$-alkoxy; 2- and 3-thienyl; 2- and 3-thienyl substituted with C$_1$–C$_6$-alkyl or halogen; 2- and 3-furyl; and 2- and 3-furyl substituted with C$_1$–C$_6$-alkyl;

R$_5$ and R$_6$ are independently selected from hydrogen, C$_1$–C$_6$-alkyl, aryl, or R$_5$ and R$_6$ may be combined to represent a —(CH$_2$—)$_{3-5}$— radical;

R$_7$ is selected from hydrogen or a group selected from C$_1$–C$_6$-alkyl, C$_3$–C$_8$-alkenyl, C$_3$–C$_8$-cycloalkyl and aryl; and R$_8$ is selected from hydrogen, C$_1$–C$_6$ alkyl and aryl.

The anthraquinone colorant compounds having formula (II) have good color strength, good solubility in the reactive monomers, good light-fastness, and exhibit outstanding thermal stability. They also are neutral blue in color and are very useful in preparing combination shades with yellow and red colorants compared to known vinyl functionalized anthraquinone colorants such as those disclosed in U.S. Pat. No. 5,055,602.

A fifth embodiment of the present invention pertains to a coating composition comprising (i) one or more polymerizable vinyl compounds, (ii) one or more of the colorant compounds of formula (II) described above, and (iii) a photoinitiator. A sixth embodiment of the present invention pertains to a polymeric composition, typically a coating, comprising a polymer of one or more acrylic acid esters, one or more methacrylic acid esters and/or other polymerizable vinyl compounds, having copolymerized therein one or more of the colorant compounds of formula (II) described above.

DETAILED DESCRIPTION

The hydroxy-functionalized, blue, anthraquinone, colorant compounds of the present have general formula (I):

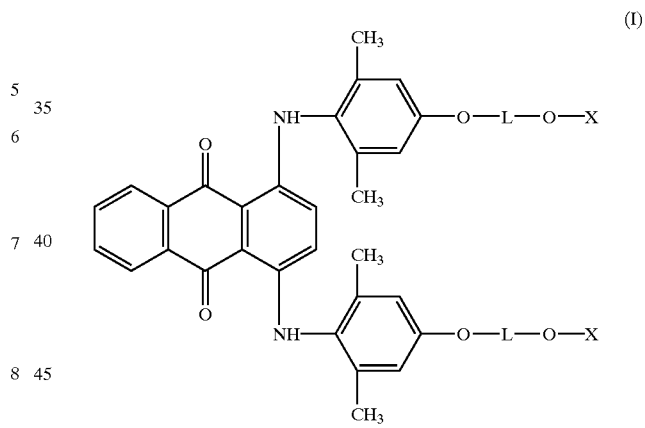

(I)

wherein L is a linking group selected from C$_2$–C$_8$-alkylene, —(—CH$_2$CH$_2$O—)$_n$—CH$_2$CH$_2$— and —CH$_2$-cyclohexylene-4-CH$_2$—, wherein n is 1 or 2; and X is hydrogen or the residue of an acylating agent. The term "C$_2$–C$_8$-alkylene" is used to denote straight- or branched-chain, divalent, hydrocarbon radicals which contain 2–8 carbon atoms which may be substituted with at least one group selected from C$_1$–C$_6$-alkoxy, halogen, hydroxy, aryl or C$_2$–C$_6$-alkanoyloxy. The colorant compounds of formula (I) wherein X is hydrogen may be acylated to produce polyester reactive groups. Examples of the acylating agent residues which X may represent include —OCOC$_1$–C$_6$-alkyl, —OCO$_2$C$_1$–C$_6$-alkyl, —COC$_1$–C$_6$-aryl and —CONHC$_1$–C$_6$-alkyl and —CONH-aryl, wherein C$_1$–C$_6$ alkyl and aryl are defined below. L preferably is selected from —CH$_2$CH$_2$— or —CH$_2$CH(CH$_3$)— and X is hydrogen.

The terms "C$_1$–C$_6$-alkoxy" and "C$_2$–C$_6$-alkanoyloxy" are used to represent the groups -O-C$_1$–C$_6$-alkyl and —OCOC- $C_6$-alkyl, respectively, wherein "$C_1$–$C_6$-alkyl" denotes a saturated hydrocarbon which contains 1–6 carbon atoms, which may be straight- or branch-chained, unsubstituted or substituted with one or more groups selected from halogen, $C_1$–$C_6$-alkoxy such as methoxy and ethoxy, phenyl, hydroxy, and $C_2$–$C_6$-alkanoyloxy such as acetyloxy and propionyloxy. The term "halogen" refers to fluorine, chlorine, bromine and iodine with chlorine and bromine being the preferred halogen atoms. The term "aryl" is used to represent phenyl and phenyl substituted with $C_1$–$C_6$-alkyl, $C_1$–$C_6$-alkoxy and halogen.

The colorant compounds of Formula (I) may be prepared according to a plurality of procedures generally known to those skilled in the art. For example, 1,4-bis-(2,6-dimethyl4-hydroxyanilino)anthraquinone of formula (III) may be reacted with: (A) an alkanol halide (IV) according to Scheme A; (B) an epoxide (V) according to Scheme B; or, preferably, (C) an alkylene carbonate (VI) according to Scheme C.

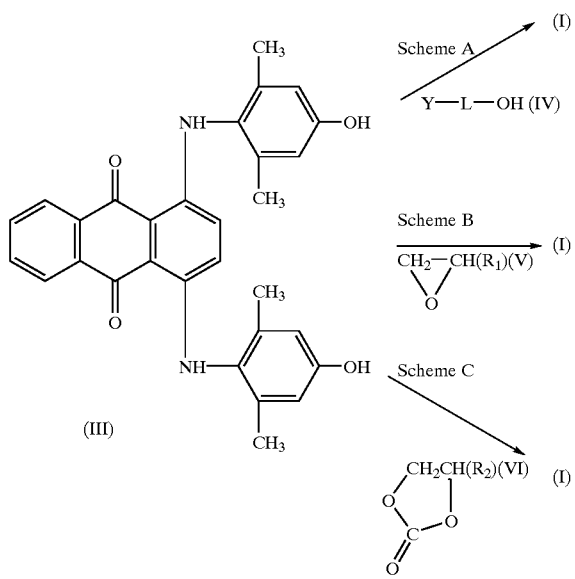

In Scheme A, the reactive alkanol halide (IV), i.e., wherein Y is halogen, preferably is an alkanol chloride, bromide or iodide. The Scheme A reaction typically is carried out in polar aprotic solvents such as N,N-dimethylformamide (DMF), N,N-dimethylacetamide (DMAC), N-methyl-2-pyrrolidinone (NMP), sulfolane, and the like, in the presence of a base such as alkali metal carbonates, alkali metal bicarbonates, tertiary amines or cyclic nitrogen-containing compounds such as 1,5-diazabicyclo[4.3.0]-non-5-ene (DBN), 1,8-diazabicyclo[5.4.0]undec-7-ene (DBU) and the like. The reaction may sometimes be facilitated by the presence of a catalytic amount of an alkali metal bromide, alkali metal iodide and/or conventional phase catalysts, e.g., tetraalkylammonium halides such as a chloride or bromide. The reactions usually are carried out at temperatures between about 50° C. and about 150° C., preferably about 90° C. to about 125° C.

In Scheme B, anthraquinone compound (III) is reacted with an epoxide (V), wherein $R_1$ is H, $CH_3$, $CH_2OH$ or aryl, using known reaction conditions for reacting aromatic hydroxy groups such as phenolic groups with epoxides. The reaction normally is carried out in the presence of a base to produce the aromatic phenoxide anion which then is reacted with the desired epoxide at temperatures of from about 0° C. to 100° C. in the presence of solvents which do not react with the epoxides under these reaction conditions. In Scheme C, anthraquinone compound (III) is reacted with an alkylene carbonate (VI), wherein $R_2$ is H or $CH_3$ to produce colorants I. This route is preferable to Schemes A and B because it circumvents the handling of haloalkanol and epoxides that are, in general, more toxic than the alkylene carbonates. These reactions are facilitated by the presence of bases such as those mentioned above for Scheme A and/or by the presence of an alkali metal halide, tetraalkylammonium halide or tetraalkylammonium hydroxide. The reactions typically are carried out by heating intermediate (III) with at least two molecular equivalent amounts of ethylene or propylene carbonate. Excess alkylene carbonate also may be used as the solvent or a co-solvent may be added. In particular, ethylene glycol and propylene glycol have been found to be effective co-solvents for the preparation of (II). Temperatures of from about 100° C. to about 175° C. normally are employed, with temperatures of from about 125° C. to about 160° C. being preferable.

The polyester component of the second embodiment of the present invention, i.e., a molding or extrusion grade polyester having reacted therewith or copolymerized therein at least one of the compounds of formula (I), may be any thermoplastic polyester having an inherent viscosity of at least about 0.4 d/g. Typical molding or extrusion grade polyester compositions are comprised of:

(i) diacid residues comprising at least 75 mole percent terephthalic acid residues;

(ii) diol residues comprising at least 75 mole percent ethylene glycol residues, wherein the total diacid residues and total diol residues each equals 100 mole percent; and (iii) colorant residues of at least one of the anthraquinone compounds of formula (I).

Up to 25 mole percent of the diacid residues and/or diol residues may be represented by one or more diacid and/or diol residues other than terephthalic acid and ethylene glycol residues. Examples of other diacid residues which may be used include isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalenedicarboxylic acid and other known dicarboxylic acids residues. The diacid residues may be derived from the diacid form of the dicarboxylic acid or from functional derivatives thereof such as the dimethyl, diethyl, bis-(2-hydroxyethyl), or dipropyl ester of the dicarboxylic acid. The anhydrides or acid halides of these acids also may be employed where practical.

Examples of alternative diol residues which may be present in the polyesters include residues derived from 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, 1,3-cyclohexanedimethanol, Z,8-bis(hydroxymethyl)-tricyclo-[5.2.1.0]decane wherein Z represents 3, 4, or 5; and diols containing one or more oxygen atoms in the chain, e.g., diethylene glycol, triethylene glycol, dipropylene glycol, tripropylene glycol and the like. In general, these diols contain 2 to 18, preferably 2 to 8 carbon atoms. Cycloaliphatic diols can be employed in their cis or trans configuration or as mixtures of both forms. The polyesters are linear, thermoplastic, film grade compositions usually having an inherent viscosity (I.V.) of about 0.4 to about 1.2 d/g measured at 25° C. in a 60/40 ratio by weight of phenol/tetrachloroethane. The preferred polyester is unmodified poly(ethylene terephthalate) and poly (ethylene terephthalate) modified with up to about 5 mole percent (of a total of 200 mole percent) of diacid residues and/or diol residues other than terephthalic acid and/or ethylene gylcol residues.

The linear polyesters may be prepared according to polyester-forming conditions well known in the art. For example, a mixture of one or more dicarboxylic acids, preferably aromatic dicarboxylic acids, or ester forming derivatives thereof, and one or more diols may be heated in the presence of esterification and/or polyesterification catalysts at temperatures in the range of about 150° C. to about 300° C., and pressures of atmospheric to about 0.2 mm Hg. Normally, the dicarboxylic acid or derivative thereof is esterified or transesterified with the diol(s) at atmospheric pressure and at a temperature at the lower end of the specified range. Polycondensation then is effected by increasing the temperature and lowering the pressure while excess diol is removed from the mixture.

Typical catalyst or catalyst systems for polyester condensation are well-known in the art. For example, the catalysts disclosed in U.S. Pat. Nos. 4,025,492; 4,136,089; 4,176,224; 4,238,593; and 4,208,527, incorporated herein by reference, are examples of the catalysts which may be used in the preparation of the colored polyester compositions of the present invention. Additional polyester condensation catalysts are described by R. E. Wilfong, *Journal of Polymer Science*, 54(385), 1961. A preferred temperature range for a polyester condensation is about 260° C. to about 300° C.

The colored polyester composition constituting the second embodiment of the present invention colorant residues of at least one of the anthraquinone compounds of formula (I). The concentration of the colorant residues in the colored polyester compositions may vary substantially, e.g., about 100 ppmw to 5 weight percent, based on the total weight of the polyester composition, of the colorant residues. The polyester compositions useful for conversion directly into X-ray film base, e.g., by conventional extrusion methods, typically contain about 100 ppmw to 500 ppmw, preferably about 150 to about 300 ppmw of the copolymerized blue colorant compound, based on the total weight of the colored polyester composition. The colored polyester composition includes color concentrate compositions wherein the polyester described above contains higher levels of the residues of at least one colorant compound of formula (I), e,g, about 0.05 to 2 weight percent, based on the total weight of the polyester color concentrate composition. This color concentrate may be used to color the described polyester by melt blending and extruding to provide a colored X-ray or photographic film base preferably containing about 100 to 500 ppmw, most preferably about 150 to about 300 ppmw.

The third embodiment of the present invention concerns a shaped or extruded article prepared from one of the colored polyester compositions described above. More specifically, the third embodiment is represented by an X-ray film element comprising a film base comprised of a polyester having reacted therewith or copolymerized therein at least one of the compounds of formula (I), i.e., containing the residue of at least one of the compounds of formula (I). The preferred film base contains about 100 to 500 ppmw, most preferably about 150 to about 300 ppmw based on the weight of the polyester and colorant residues.

The fourth embodiment of the present invention concerns novel anthraquinone colorant compounds having the formula:

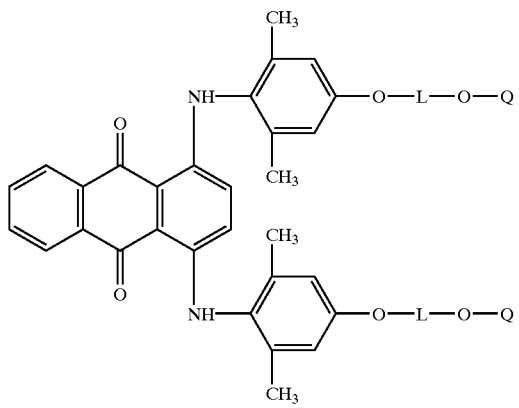

(II)

in L is a linking group selected from $C_2$–$C_8$-alkylene, $-(-CH_2CH_2O-)_n-CH_2CH_2-$ and $-CH_2$-cyclohexylene-4-$CH_2-$, wherein n is 1 or 2; and Q is a photopolymerizable group selected from organic radicals having the formulae:

$-COC(R_3)=CH-R_4$,     1

$-CONHCOC(R_3)=CH-R_4$,     2

$-CONH-C_1-C_6\text{-alkylene } OCOC(R_3)=CH-R_4$,     3

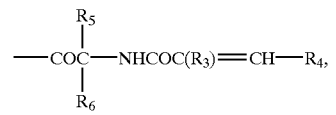     4

     5

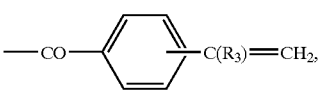     6

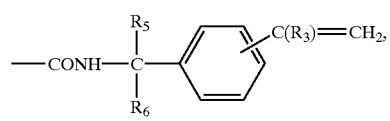     7

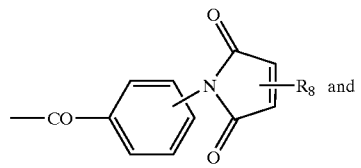     8

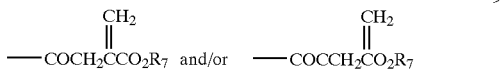     9 wherein $R_3$ is selected from hydrogen or $C_1$–$C_6$-alkyl;

$R_4$ is selected from hydrogen; $C_1$–$C_6$-alkyl; phenyl; phenyl substituted with one or more groups selected from $C_1$–$C_6$-alkyl, $C_1$–$C_6$-alkoxy, $-N(C_1$–$C_6$-alkyl$)_2$, nitro, cyano, $C_2$–$C_6$-alkoxycarbonyl, $C_2$–$C_6$-alkanoyloxy and halogengen; 1- and 2-naphthyl; 1- and 2-naphthyl substituted with $C_1$–$C_6$-alkyl or $C_1$–$C_6$- alkoxy; 2- and 3-thienyl; 2- and 3-thienyl substituted with $C_{1-6}$-alkyl or halogen; 2- and 3-furyl; and 2- and 3-furyl substituted with $C_{1-6}$-alkyl;

$R_5$ and $R_6$ are independently selected from hydrogen, $C_1$–$C_6$-alkyl, aryl, or $R_5$ and $R_6$ may be combined to represent a —($CH_2$—$)_{3-5}$- radical;

$R_7$ is selected from hydrogen or a group selected from $C_1$–$C_6$-alkyl, $C_3$–$C_8$-alkenyl, $C_3$–$C_8$-cycloalkyl and aryl; and $R_8$ is selected from hydrogen, $C_1$–$C_6$ alkyl and aryl. Q preferably is a group having the formula —COC($R_3$)=$CH_2$ or

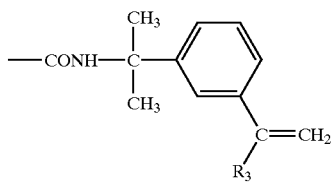

wherein $R_3$ is hydrogen or methyl.

As used in the above definition of the radicals represented by Q, the terms "$C_1$–$C_6$-alkyl", "$C_1$–$C_6$-alkoxy", "$C_2$–$C_6$-alkanoyloxy", "aryl" and "halogen" have the meaning given above. The term "$C_2$–$C_6$-alkoxycarbonyl" refers to the group —$CO_2C_1$–$C_5$-alkyl. The term "$C_3$–$C_8$-alkenyl" designates an aliphatic hydrocarbon radical containing at least one double bond and from three to eight carbon atoms. The term $C_3$–$C_8$-cycloalkyl refers to a saturated cyclic hydrocarbon radical containing three to eight carbon atoms.

The vinyl-functionalized colorant compounds of formula (II) are prepared by reacting the blue diol compounds of formula (I) with an acylating agents having formulae 1'–9':

 1'

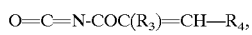 2'

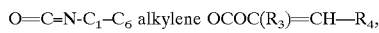 3'

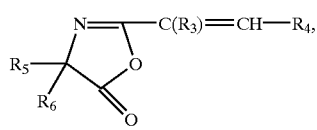 4'

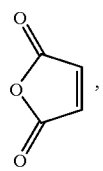 5'

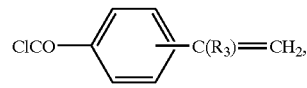 6'

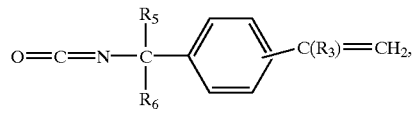 7'

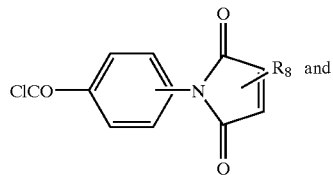 8'

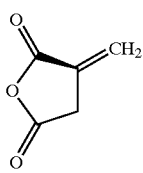 9' wherein $R_3$, $R_4$, $R_5$, $R_6$, $R_8$ are defined above.

The anthraquinone colorant compounds of formula (II) which contain vinyl or substituted vinyl groups are polymerizable or copolymerizable, preferably by free radical mechanisms, said free radicals being generated by exposure to UV light by methods known in the art of preparing UV-cured resins. Polymerization can be facilitated by the addition of photoinitiators. The colored polymeric materials normally are prepared by dissolving the functionalized colorants containing copolymerizable groups in a polymerizable vinyl monomer with or without another solvent and then combining with an oligomeric or polymeric material which contains one or more vinyl or substituted vinyl groups.

The fifth embodiment of the present invention is a coating composition comprising (i) one or more polymerizable vinyl compounds, i.e., vinyl compounds which are copolymerizable with the colorant compounds of formula (II), (ii) one or more of the colorant compounds of formula (II), and (iii) at least one photoinitiator. The polymerizable vinyl compounds useful in the present invention contain at least one unsaturated group capable of undergoing polymerization upon exposure to UV radiation in the presence of a photoinitiator, i.e., the coating compositions are radiation-curable. Examples of such polymerizable vinyl compounds include acrylic acid, methacrylic acid and their anhydrides; crotonic acid; itaconic acid and its anhydride; cyanoacrylic acid and its esters; esters of acrylic and methacrylic acids such as allyl, methyl, ethyl, n-propyl, isopropyl, butyl, tetrahydrofurfuryl, cyclohexyl, isobornyl, n-hexyl, n-octyl, isooctyl, 2-ethylhexyl, lauryl, stearyl, and benzyl acrylate and methacrylate; and diacrylate and dimethacrylate esters of ethylene and propylene glycols, 1,3-butylene glycol, 1,4-butanediol, diethylene and dipropylene glycols, triethylene and tripropylene glycols, 1,6-hexanediol, neopentyl glycol, polyethylene glycol, and polypropylene glycol, ethoxylated bisphenol A, ethoxylated and propoxylated neopentyl glycol; triacrylate and trimethacrylate esters of tris-(2-hydroxyethyl)isocyanurate, trimethylolpropane, ethoxylated and propoxylated trimethylolpropane, pentaerythritol, glycerol, ethoxylated and propoxylated glycerol; tetraacrylate and tetramethacrylate esters of pentaerythritol and ethoxylated and propoxylated pentaerythritol; acrylonitrile; vinyl acetate; vinyl toluene; styrene; N-vinyl pyrrolidinone; alpha-methyl-styrene; maleate/fumarate esters; maleic/fumaric acid; crotonate esters, and crotonic acid.

The polymerizable vinyl compounds useful in the present invention include polymers which contain unsaturated groups capable of undergoing polymerization upon exposure to UV radiation in the presence of a photoinitiator. The preparation and application of these polymerizable vinyl compounds are well known to those skilled in the art as described, for example, in *Chemistry and Technology of UV and EB Formulation for Coatings, Inks, and Paints*, Volume II: Prepolymers and Reactive Diluents, G. Webster, editor, John Wiley and Sons, London, 1997. Examples of such polymeric, polymerizable vinyl compounds include acrylated and methacrylated polyesters, acrylated and methacrylated polyethers, acrylated and methacrylated epoxy polymers, acrylated or methacrylated urethanes, acrylated or methacrylated polyacrylates (polymethacrylates), and unsaturated polyesters. The acrylated or methacrylated polymers and oligomers typically are combined with monomers which contain one or more acrylate or methacrylate groups, e.g., monomeric acrylate and methacrylate esters, and serve as reactive diluents. The unsaturated polyesters, which are prepared by standard polycondensation techniques known in the art, are most often combined with either styrene or other monomers, which contain one or more acrylate or methacrylate groups and serve as reactive diluents. A second embodiment for the utilization of unsaturated polyesters that is known to the art involves the combination of the unsaturated polyester with monomers that contain two or more vinyl ether groups or two or more vinyl ester groups (WO 96/01283, WO 97/48744, and EP 0 322 808).

The coating compositions of the present invention optionally may contain one or more added organic solvents if desired to facilitate application and coating of the compositions onto the surface of substrates. Typical examples of suitable solvents include, but are not limited to ketones, alcohols, esters, chlorinated hydrocarbons, glycol ethers, glycol esters, and mixtures thereof. Specific examples include, but are not limited to acetone, 2-butanone, 2-pentanone, ethyl acetate, propyl acetate, isopropyl acetate, butyl acetate, isobutyl acetate, ethylene glycol diacetate, ethyl 3-ethoxypropionate, methyl alcohol, ethyl alcohol, propyl alcohol, isopropyl alcohol, butyl alcohol, ethylene glycol, propylene glycol, ethylene glycol monomethyl ether, ethylene glycol monoethyl ether, ethylene glycol monopropyl ether, ethylene glycol monobutyl glycol, diethylene glycol monomethyl ether, diethylene glycol monoethyl ether, diethylene glycol monobutyl ether, propylene glycol monomethyl ether, diethylene glycol monobutyl ether acetate, diethylene glycol monoethyl ether acetate, ethylene glycol monobutyl ether acetate, propylene glycol monomethyl ether acetate, methylene chloride, chloroform, and mixtures thereof. The amount of added or extraneous solvent which may be present in our novel coating compositions may be in the range of about 1 to 70 weight percent, more typically about 1 to 25 weight percent, based on the total weight of the coating composition.

Certain polymerizable vinyl monomers may serve as both reactant and solvent. These contain at least one unsaturated group capable of undergoing polymerization upon exposure to UV radiation in the presence of a photoinitiator. Specific examples include, but are not limited to: methacrylic acid, acrylic acid, ethyl acrylate and methacrylate, methyl acrylate and methacrylate, hydroxyethyl acrylate and methacrylate, diethylene glycol diacrylate, trimethylolpropane triacrylate, 1,6 hexanediol di(meth)acrylate, neopentyl glycol diacrylate and methacrylate, vinyl ethers, divinyl ethers such as diethyleneglycol divinyl ether, 1,6-hexanediol divinyl ether, cyclohexanedimethanol divinyl ether, 1,4-butanediol divinyl ether, triethyleneglycol divinyl ether, trimethylolpropane divinyl ether, and neopentyl glycol divinyl ether, vinyl esters, divinyl esters such as divinyl adipate, divinyl succinate, divinyl glutarate, divinyl 1,4-cyclohexanedicarboxylate, divinyl 1,3-cyclohexanedicarboxylate, divinyl isophthalate, and divinyl terephthalate, N-vinyl pyrrolidone, and mixtures thereof.

In addition, the compositions of the present invention may be dispersed in water rather than dissolved in a solvent to facilitate application and coating of the substrate surface. In the water-dispersed compositions of the present invention a co-solvent is optionally used. Typical examples of suitable cosolvents include but are not limited to acetone, 2-butanone, methanol, ethanol, isopropyl alcohol, ethylene glycol monomethyl ether, ethylene glycol monoethyl ether, ethylene glycol monopropyl ether, and ethylene glycol monobutyl ether, ethylene glycol, and propylene glycol. Typical examples of water-soluble ethylenically unsaturated solvents include but are not limited to: methacrylic acid, acrylic acid, N-vinyl-pyrrolidone, 2-ethoxyethyl acrylate and methacrylate, polyethylene glycol dimethacrylate, polypropylene glycol monoacrylate and monomethacrylate, and mixtures thereof. The amount of suitable aqueous organic solvent (i.e., organic solvent and water) in the dispersed coating compositions of the present invention is about 10 to about 90 weight percent, preferably about 75 to about 90 weight percent of the total coating composition.

The coating compositions of the present invention contain one or more of the reactive anthraquinone colorant compounds of formula (II). The concentration of the colorant compound or compounds may be from about 0.005 to 30.0, preferably from about 0.05 to 15.0, weight percent based on the weight of the polymerizable vinyl compound(s) present in the coating composition, i.e., component (i) of the coating compositions. The coating compositions of the present invention normally contain a photoinitiator. The amount of photoinitiator typically is about 1 to 15 weight percent, preferably about 3 to about 5 weight percent, based on the weight of the polymerizable vinyl compound(s) present in the coating composition. Typical photoinitiators include benzoin and benzoin ethers such as marketed under the tradenames ESACURE BO, EB1, EB3, and EB4 from Fratelli Lamberti; VICURE 10 and 30 from Stauffer; benzil ketals such as 2,2-dimethoxy-1,2-diphenylethan-1-one (IRGACURE 651), 2-hydroxy-2-methyl-1-phenylpro-pan-1'-one (IRGACURE 1173), 2-methyl-2-morpholino-1-(p-methylthio-phenyl)propan-1-one (IRGACURE 907), alpha-hydroxyalkylphenones such as (1-hydroxycyclohexyl) (phenyl)methanone (IRGACURE 184), 2-benzyl-2-(dimethylamino)-1-(4-morpholinophenyl)butan-1-one (IRGACURE 369), 2-hydroxy-2-methyl-1'-phenylpropan-1-one IRGACURE 1173) from Ciba Geigy, Uvatone 8302 by Upjohn; alpha, alpha-dialkoxyacetophenone derivatives such as DEAP and UVATONE 8301 from Upjohn; DAROCUR 116, 1173, and 2959 by Merck; and mixtures of benzophenone and tertiary amines In pigmented coating compositions, the rate of cure can be improved by the addition of a variety of phosphine oxide photoinitiaters such as bis(2,4,6-trimethylbenzoyl)-phenylphosphine oxide (Irganox 819), Irgacure 819, 1700, and 1700 and phosphine oxide mixtures such as a 50/50 by weight mixtures of IRGACURE 1173 and 2,4,6-trimethyl-benzoyldiphenylphosphine oxide (DAROCUR 4265) from Ciba. Further details regarding such photoinitiators and curing procedures may be found in the published literature such as U.S. Pat. No. 5,109,097, incorporated herein by reference. Depending upon the thickness of the coating (film), product formulation, photoinitiator type, radiation flux, and source of radiation, exposure times to ultraviolet radiation of about 0.5 second to about 30 minutes (50–5000 mJ/square cm) typically are required for curing. Curing also can occur from solar radiation, i.e., sunshine.

The coating compositions of the present invention may contain one or more additional components typically present in coating compositions. Examples of such additional components include leveling, rheology, and flow control agents such as silicones, fluorocarbons or cellulosics; flatting agents; pigment wetting and dispersing agents; surfactants; ultraviolet (UV) absorbers; UV light stabilizers; tinting pigments; defoaming and antifoaming agents; anti-settling, anti-sag and bodying agents; anti-skinning agents; anti-flooding and anti-floating agents; fungicides and mildew-cides; corrosion inhibitors; thickening agents; and/or coalescing agents. The coating compositions of the present invention also may contain non-reactive modifying resins. Typical non-reactive modifying resins include homopolymers and copolymers of acrylic and methacrylic acid; homopolymers and copolymers of alkyl esters of acrylic and methacrylic acid such as methyl, ethyl, n-propyl, isopropyl, butyl, tetrahydrofurfuryl, cyclohexyl, isobornyl, n-hexyl, n-octyl, isooctyl, 2-ethylhexyl, lauryl, stearyl, and benzyl acrylate and methacrylate; acrylated and methacrylated urethane, epoxy, and polyester resins, silicone acrylates, cellulose esters such as cellulose acetate butyrates, cellulose acetate, propionates, nitrocellulose, cellulose ethers such as methyl cellulose, ethyl cellulose, hydroxypropyl cellulose, and hydroxypropyl methyl cellulose.

Typical plasticizers include alkyl esters of phthalic acid such as dimethyl phthalate, diethyl phthalate, dipropyl phthalate, dibutyl phthalate, and dioctyl phthalate; citrate esters such as triethyl citrate and tributyl citrate; triacetin and tripropionin; and glycerol monoesters such as Eastman 18–04, 18–07, 18–92 and 18–99 from Eastman Chemical Company. Specific examples of additional additives can be found in Raw Materials Index, published by the National Paint & Coatings Association, 1500 Rhode Island Avenue, N.W., Washington, D.C. 20005.

The sixth embodiment of the present invention pertains to a polymeric composition, typically a polymeric coating, comprising a polymer of one or more acrylic acid esters, one or more methacrylic acid esters and/or other polymerizable vinyl compounds, having copolymerized therein one or more of the anthraquinone colorant compounds of formula (II). The colored polymeric compositions provided by our invention may be prepared from the coating compositions described above and typically contain from about 0.005 to 30.0 weight percent, preferably from about 05 to 15.0 weight percent, of the reactive or polymerized residue of one or more of the colorant compounds of formula (II) based on the weight of the composition or coating. The novel polymeric coatings may have a thickness of about 2.5 to 150 microns, more typically about 15 to 65 microns.

The polymeric coatings of the present invention typically have a solvent resistance of at least 100 MEK double rubs using ASTM Procedure D-3732; preferably a solvent resistance of at least about 200 double rubs. Such coatings also typically have a pencil hardness of greater than or equal to F using ASTM Procedure D-3363; preferably a pencil hardness of greater than or equal to H. The coating compositions can be applied to substrates with conventional coating equipment. The coated substrates are then exposed to radiation such as ultraviolet light in air or in nitrogen which gives a cured finish. Mercury vapor or Xenon lamps are applicable for the curing process. The coatings of the present invention can also be cured by electron beam.

The radiation-curable coating compositions of this invention are suitable as adhesives and coatings for such substrates as metals such as aluminum and steel, plastics, glass, wood, paper, and leather. On wood substrates the coating compositions may provide both overall transparent color and grain definition. Various aesthetically-appealing effects can be achieved thereby. Due to reduced grain raising and higher film thicknesses, the number of necessary sanding steps in producing a finished wood coating may be reduced when using the colored coating compositions of the invention rather than conventional stains. Coating compositions within the scope of our invention may be applied to automotive base coats where they can provide various aesthetically-appealing effects in combination with the base coats and color differences dependent on viewing angle (lower angles create longer path lengths and thus higher observed color intensities). This may provide similar styling effects as currently are achieved with metal flake orientation in base coats.

Various additional pigments, plasticizers, and stabilizers may be incorporated to obtain certain desired characteristics in the finished products. These are included in the scope of the invention.

EXAMPLES

The anthraquinone colorant compounds, polyester compositions and coating compositions provided by the present invention are further illustrated by the following examples.

Example 1

A mixture of 1,4-bis(2',6'-dimethyl-4'-hydroxyanilino) anthraquinone (4.78 g, 0.01 mol) (U.S. Pat. No. 3,918,976), potassium iodide (3.0 g), potassium carbonate (1.38 g), ethylene carbonate (10.6 g, 0.12 m) and ethylene glycol (35 mL) was heated and stirred at about 150° C. for about one hour in an oil bath. Thin-layer chromatography (50/50 tetrahydrofuran/cyclohexane) showed one blue spot that had a lower Rf value and no spot for starting material. After being cooled, the reaction mixture was treated with methanol and stirred to precipitate the blue product, which was collected by filtration, washed with methanol, washed with hot water and then washed again with methanol to facilitate drying. The blue colorant weighed 3.49 g (62% of the theoretical yield) and field desorption mass spectral analysis confirmed the structure:

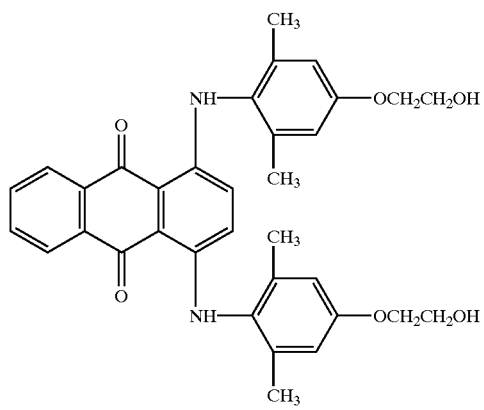

Additional examples (Examples 2–10) of the anthraquinone colorant compounds of formula (I) are presented in Table I.

TABLE I

| Example No. | —L— |
|---|---|
| 2 | —CH$_2$CH(OH)— |
| 3 | —CH$_2$C(CH$_3$)$_2$CH$_2$— |
| 4 | —CH$_2$CH(C$_6$H$_5$)— |
| 5 | —CH$_2$CH$_2$CH$_2$— |
| 6 | —(CH$_2$)$_4$— |
| 7 | —CH$_2$CH$_2$OCH$_2$CH$_2$— |
| 8 | —(CH$_2$CH$_2$O)$_2$CH$_2$CH$_2$— |
| 9 | —CH$_2$CH(OH)CH$_2$— |
| 10 | —CH$_2$C$_6$H$_{10}$-4-CH$_2$— |

Example 11

The following materials were placed in a 500 mL, three-necked, round-bottom flask:

97.0 g (0.50 mol) dimethyl terephthalate 62.0 g (1.0 mol) ethylene glycol 2.0 mL of an n-butanol solution containing 0.3 g of titanium tetraisopropoxide per 100 mL of solution;

3.1 mL of an ethylene glycol solution containing 0.79 g of antimony triacetate per 100 mL of solution; and 0.0288 g of blue colorant of Example 1 (300 ppm).

The flask was equipped with a nitrogen inlet, stirrer, vacuum outlet and condensing flask and contents were stirred and heated in a Belmont metal bath for about 45 minutes at 200° C. The temperature was increased to about 210° C. for 65 minutes with a nitrogen sweep over the reaction mixture. The temperature was increased to about 268° C. over about 30 minutes and then 0.40 mL of an ethylene glycol solution of a mixed phosphorous ester composition (Merpol A) (0.0914 g Merpol A/mL of solution) was added. The pressure was reduced from atmospheric to about 120 torr over 5 minutes and held at about 268° C. for 50 minutes. Polycondensation was completed by increasing the temperature to about 285° C., reducing the pressure to about 8 torr over 5 minutes, holding this temperature and pressure for about 25 minutes, reducing the pressure to about 0.5 torr over about 1 minute and holding for 20 minutes. The resulting blue polyester had an inherent viscosity of 0.596 as measured in a 60/40 ratio by weight of phenol/tetrachloroethane at a concentration of 0.5 g per 100 mL. After grinding the polymer in a Wiley mill and passing the solid through a 3 mm screen, a blue tinted film having a thickness of 381 micron (15 mil) was prepared by compression molding a portion of the polyester composition. No evidence of color volitalization or sublimation was noted during the entire polymerization reaction in the collected distillates comprising methanol and ethylene glycol. The film has desirable light transmission properties for use as a blue tinted X-ray film base.

Comparative Example 1

The procedure of Example I was repeated exactly except that the prior art dye 1,4-bis-2',6'-diethylanilino) anthraquinone (U.S. Pat. No. 3,488,195) was used. In contrast to the colorant of Example I, this colorant volatilized and colored the collected distillates blue showing that this type colorant is unsuitable for addition during polyester manufacture.

Example 12

A mixture of 1,4-bis(2',6'-dimethyl-4'-hydroxyanilino) anthraquinone (1.50 g, 3.13 mmol) (U.S. Pat. No. 3,918, 976), potassium iodide (1.0 g), potassium carbonate (0.45 g), propylene carbonate (3.84 g, 37.6 mmol) and propylene glycol (15 ml) was stirred and heated at 150° C. for about 2.5 hours. The mixture was allowed to cool to room temperature and methanol (50 ml) was added followed by 50 ml of water. The product was collected by filtration, washed with water and dried in air (yield 1.6, 95% of theory). FDMS supported the following expected structure:

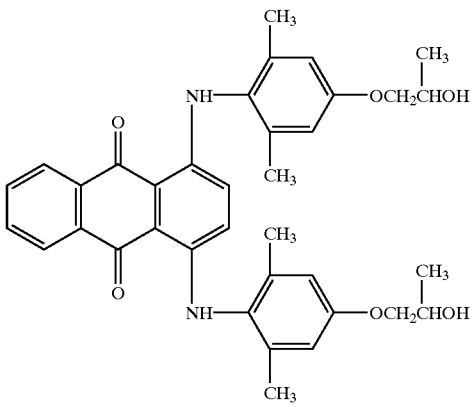

Example 13

A portion (0.6 g, 1 mmol) of the diol colorant from Example 12, 3-isopropenyl-α,α-dimethylbenzyl isocyanate (0.5 g), toluene (15 ml) and dibutyltin laurate (2 drops) were mixed and heated together with stirring to about 90° C. and held at 90° C. for about 2.0 hours. While still hot, heptane (30 ml) was added and the mixture was allowed to cool. No solid precipitated so the mixture was poured into an evaporating dish and solvent was allowed to evaporate leaving a semi-solid, dark blue product which solidified upon treatment with some heptane. The solid product was separated from the heptane by filtration, washed with heptane, and dried in air (yield=0.75 g, 75.3% of theory). FDMS supported the structure:

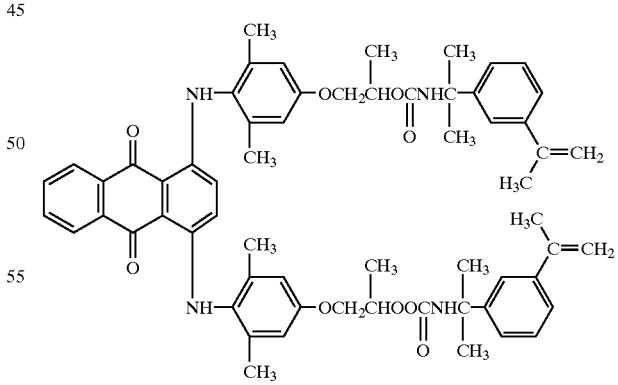

Examples 14–31

Additional examples of the vinyl functionalized anthraquinone colorant compounds of formula (II) are presented in Table II.

TABLE II

| Example No. | L | Q |
|---|---|---|
| 14 | —CH$_2$CH$_2$— | —COC(CH$_3$)=CH$_2$ |
| 15 | —CH$_2$CH$_2$— | —CONHC(CH$_3$)$_2$-1,3-C$_6$H$_4$—C(CH$_3$)=CH$_2$ |
| 16 | —CH$_2$CH(CH$_3$)— | —COC(CH$_3$)=CH$_2$ |
| 17 | —CH$_2$CH(CH$_3$)— | —COCH=CH$_2$ |
| 18 | —CH$_2$CH$_2$— | —COCH=CH$_2$ |
| 19 | —CH$_2$CH$_2$CH$_2$— | —COCH=CH—CH$_3$ |
| 20 | —CH$_2$CH(OH)CH$_2$— | —COCH=CH—C$_6$H$_5$ |
| 21 | —CH$_2$CH(C$_6$H$_5$)— | —COC(CH$_3$)=CH—(2-furyl) |
| 22 | —(CH$_2$)$_4$— | —COCH=CH—(2-thienyl) |
| 23 | —CH$_2$CH$_2$OCH$_2$CH$_2$— | —COC(CH$_3$)=CH$_2$ |
| 24 | —(CH$_2$CH$_2$O)$_2$—CH$_2$CH$_2$— | —CONHC(CH$_3$)$_2$-1,3-C$_6$H$_4$—C(CH$_3$)=CH$_2$ |
| 25 | —CH$_2$—(1,4-C$_6$H$_4$)—CH$_2$— | —COCH=CH—CO$_2$H |
| 26 | —CH$_2$CH$_2$— | —CO-1,4-C$_6$H$_4$—CH=CH$_2$ |
| 27 | —CH$_2$CH$_2$— | —COC(CH$_3$)$_2$NHCOC(CH$_3$)=CH$_2$ |
| 28 | —CH$_2$CH$_2$— | —CONHCOC(CH$_3$)=CH$_2$ |
| 29 | —CH$_2$CH$_2$— | —CO—(4-C$_6$H$_4$)—N(maleimide) |
| 30 | —CH$_2$CH$_2$— | —COCH$_2$C=(CH$_2$)CO$_2$CH$_3$ |
| 31 | —CH$_2$CH$_2$— | —COCH=CH—CO$_2$C$_2$H$_5$ |

Samples of the coating compositions may be used to coat glass plates using a knife blade. The wet film thickness typically is about 15 to 75 microns (0.6 to 3.0 mils). Any solvent present is evaporated to give a clear, somewhat tacky film. Prior to exposure to UV radiation, each film is readily soluble in organic solvents. The dried film on the glass plate is exposed to UV radiation from a 200 watt per inch medium pressure mercury vapor lamp housed in an American Ultraviolet Company instrument using a belt speed of 25 ft. per minute. One to five passes under the lamp normally provides a crosslinked coating with maximum hardness and solvent resistance.

Each cured coating (film) may be evaluated for Konig Pendulum Hardness (ASTM D4366 DIN 1522), solvent resistance by the methyl ethyl ketone double-rub test, and solubility in acetone before and after exposure to UV radiation. The damping time for Konig Pendulum Hardness on uncoated glass is 250 seconds; coatings with hardness above 100 seconds are generally considered hard coatings. The methyl ethyl ketone (MEK) double rub test is carried out in accordance with ASTM Procedure D-3732 by saturating a piece of cheese cloth with methyl ethyl ketone, and with moderate pressure, rubbing the coating back and forth. The number of double rubs is counted until the coating is removed. The acetone solubility test is carried out by immersing a dry, pre-weighed sample of the cured film in acetone for 48 hours at 25° C. The film is removed, dried for 16 hours at 60° C. in a forced-air oven, and reweighed. The weight percent of the insoluble film remaining is calculated from the data.

The coatings and coating compositions provided by the present invention and the preparation thereof are further illustrated by the following example. A colored, photopolymerizable composition was prepared by thoroughly mixing 0.5 g the blue dye of Example 13 with a coating composition consisting of 20 g Jägalux UV1500 polyester acrylate, 10 g of bisphenol A epoxy acrylate, 9 g dipropyleneglycol diacrylate (DPGDA), 7 g trimethylolpropane triacrylate (TMPTA), and 4 g of Darocure 1173 photoinitiator using a small Cowles mixer until the components were completely dispersed. The resulting coating composition containing 1% of the blue colorant compound is drawn down with a wire wound rod to provide a 25.4 micron (1 mil) thick coating on an oak wood panel. This panel is passed through a UV cure machine at a speed of 6.1 meters per minute (20 feet/minute) using a lamp with an intensity of 118.1 watts per cm (300 watts per inch). Konig Pendulum Hardness measurements (ASTM D4366 DIN 1522) conducted on the coated panel typically show no significant loss of hardness due to incorporation of the dye.

The invention has been described in detail with particular reference to preferred embodiments thereof, but it will be understood that variations and modifications can be effected within the spirit and scope of the invention.

We claim:

1. A copolymerizable, thermally stable, blue anthraquinone colorant compound having the formula:

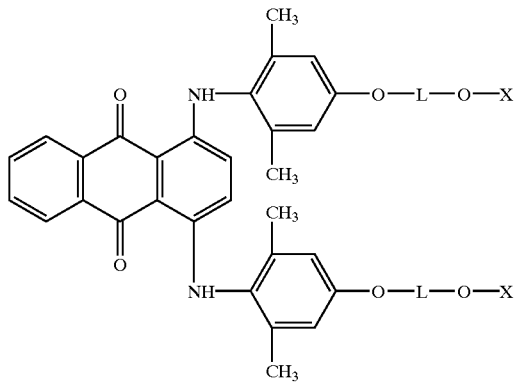

wherein L is a linking group selected from $C_2$–$C_8$-alkylene, —(—$CH_2CH_2O$—)$_n$—$CH_2CH_2$— and —$CH_2$-cyclohexylene-4-$CH_2$—, wherein n is 1 or 2; and X is hydrogen or the residue of an acylating agent.

2. An anthraquinone colorant compound according to claim 1 wherein X is hydrogen or the residue of an acylating agent having the formula —$OCOC_1$–$C_6$-alkyl, —$OCO_2C_1$–$C_6$-alkyl, —$COC_1$–$C_6$-aryl and —$CONHC_1$–$C_6$-alkyl and —CONH-aryl.

3. An anthraquinone colorant compound according to claim 1 wherein X is hydrogen.

4. An anthraquinone colorant compound according to claim 1 wherein L is —$CH_2CH_2$— or —$CH_2CH(CH_3)$— and X is hydrogen.

5. A molding or extrusion grade polyester composition comprising a polyester having an inherent viscosity of at least 0.4 having reacted therewith or copolymerized therein at least one of the anthraquinone colorant compounds defined in claim 1.

6. A molding or extrusion grade polyester composition according to claim 5 having an inherent viscosity of about 0.4 to 1.2 comprising:

(i) diacid residues comprising at least 75 mole percent terephthalic acid residues;

(ii) diol residues comprising at least 75 mole percent ethylene glycol residues, wherein the total diacid residues and total diol residues each equals 100 mole percent; and (iii) colorant residues of at least one of the anthraquinone compounds having the formula:

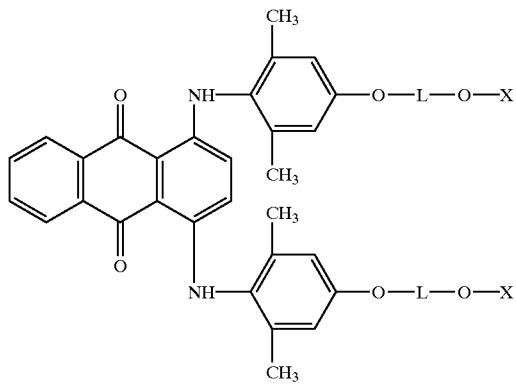

wherein L is a linking group selected from $C_2$–$C_8$-alkylene, —(—$CH_2CH_2O$—)$_n$—$CH_2CH_2$— and —$CH_2$-cyclohexylene-4-$CH_2$—, wherein n is 1 or 2; and X is hydrogen or the residue of an acylating agent.

7. A molding or extrusion grade polyester composition according to claim 6 wherein L is —$CH_2CH_2$— or —$CH_2CH(CH_3)$—, X is hydrogen, the concentration of the colorant residues is about 100 to 500 ppmw, and the polyester is selected from unmodified poly(ethylene terephthalate) and poly(ethylene terephthalate) modified with up to about 5 mole percent of diacid residues and/or diol residues other than terephthalic acid and/or ethylene gylcol residues.

8. A molding or extrusion grade polyester composition according to claim 6 wherein L is —$CH_2CH_2$— or —$CH_2CH(CH_3)$—, X is hydrogen, the concentration of the colorant residues is about 0.05 to 2 weight percent, and the polyester is selected from unmodified poly(ethylene terephthalate) and poly(ethylene terephthalate) modified with up to about 5 mole percent of diacid residues and/or diol residues other than terephthalic acid and/or ethylene gylcol residues.

9. An X-ray film element comprising a film base comprised of a polyester having reacted therewith or copolymerized therein at least one of the compounds of formula (I).

10. The X-ray film element of claim 9 wherein the polyester has an inherent viscosity of about 0.4 to 1.2 and comprises:

(i) diacid residues comprising at least 75 mole percent terephthalic acid residues;

(ii) diol residues comprising at least 75 mole percent ethylene glycol residues, wherein the total diacid residues and total diol residues each equals 100 mole percent; and (iii) 100 to 500 ppmw colorant residues of at least one of the anthraquinone compounds having the formula:

(I)

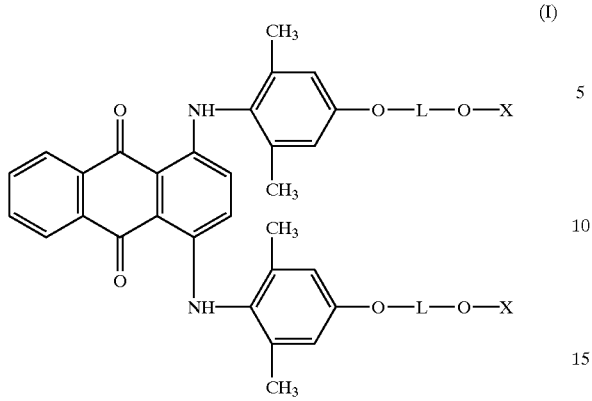

wherein L is a linking group selected from $C_2$–$C_8$-alkylene, —($CH_2CH_2O$—)$_n$—$CH_2CH_2$— and —$CH_2$-cyclohexylene-4-$CH_2$—, wherein n is 1 or 2; and X is hydrogen or the residue of an acylating agent.

11. The X-ray film element of claim 10 wherein wherein L is —$CH_2CH_2$— or —$CH_2CH(CH_3)$—, X is hydrogen, the concentration of the colorant residues is about 150 to 300 ppmw, and the polyester is selected from unmodified poly(ethylene terephthalate) and poly(ethylene terephthalate) modified with up to about 5 mole percent of diacid residues and/or diol residues other than terephthalic acid and/or ethylene gylcol residues.

12. An anthraquinone colorant compound having the formula:

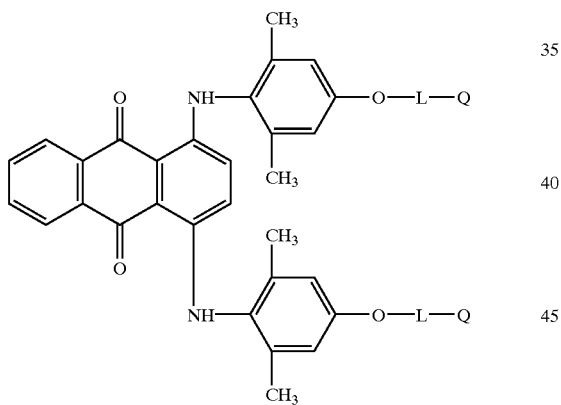

wherein L is a linking group selected from $C_2$–$C_8$-alkylene, —($CH_2CH_2O$—)$_n$—$CH_2CH_2$— and —$CH_2$-cyclohexylene-4-$CH_2$—, wherein n is 1 or 2; and Q is a photopolymerizable group selected from the radicals having the formulae

—COC($R_3$)=CH—$R_4$,  1

—CONHCOC($R_3$)=CH—$R_4$,  2

—CONH—$C_1$–$C_6$-alkylene OCOC($R_3$)=CH—$R_4$,  3

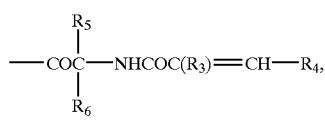  4

—COCH=CH—$CO_2R_7$,  5

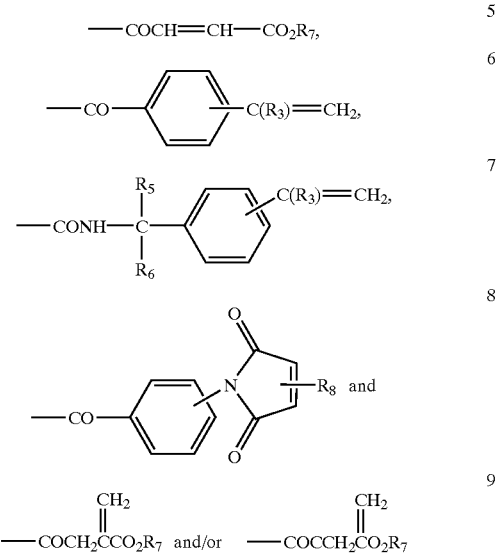

—COCH$_2\overset{CH_2}{\overset{\|}{C}}CO_2R_7$ and/or —COCCH$_2CO_2R_7$  9 wherein $R_3$ is selected from hydrogen or $C_1$–$C_6$-alkyl;

$R_4$ is selected from hydrogen; $C_1$–$C_6$-alkyl; phenyl; phenyl substituted with one or more groups selected from $C_1$–$C_6$-alkyl, $C_1$–$C_6$-alkoxy, —N($C_1$–$C_6$-alkyl)$_2$, nitro, cyano, $C_2$–$C_6$-alkoxycarbonyl, $C_2$–$C_6$-alkanoyloxy and halogen; 1- and 2-naphthyl; 1- and 2-naphthyl substituted with $C_1$–$C_6$-alkyl or $C_1$–$C_6$-alkoxy; 2- and 3-thienyl; 2- and 3-thienyl substituted with $C_1$–$C_6$-alkyl or halogen; 2- and 3-furyl; and 2- and 3-furyl substituted with $C_1$–$C_6$-alkyl;

$R_5$ and $R_6$ are independently selected from hydrogen, $C_1$–$C_6$-alkyl, aryl, or $R_5$ and $R_6$ may be combined to represent a —($CH_2$—)$_{3-5}$— radical;

$R_7$ is selected from hydrogen or a group selected from $C_1$–$C_6$-alkyl, $C_3$–$C_8$-alkenyl, $C_3$–$C_8$-cycloalkyl and aryl; and $R_8$ is selected from hydrogen, $C_1$–$C_6$ alkyl and aryl.

13. An anthraquinone colorant compound according to claim 12 wherein Q is a group having the formula —COC($R_3$)=$CH_2$ or

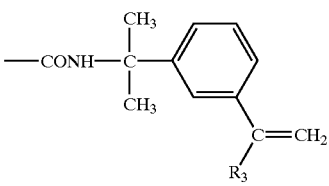

wherein $R_3$ is hydrogen or methyl.

14. An anthraquinone colorant compound according to claim 12 wherein L is —$CH_2CH_2$— or —$CH_2CH(CH_3)$— and Q is a group having the formula —COC($R_3$)=$CH_2$ or

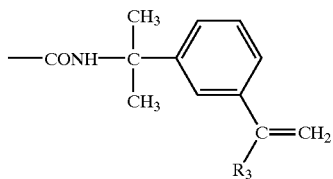

wherein $R_3$ is hydrogen or methyl.

15. A coating composition comprising (i) one or more polymerizable vinyl compounds, (ii) one or more of the colorant compounds according to claim 12, and (iii) at least one photoinitiator.

16. A coating composition according to claim 15 comprising (i) one or more polymerizable vinyl compounds, (ii) one or more of the colorant compounds of claim 12 present in a concentration of about 0.05 to 15 weight percent based on the weight of component (i), and (iii) a photoinitiator present in a concentration of about 1 to 15 weight percent based on the weight of the polymerizable vinyl compound(s) present in the coating composition.

17. A coating composition according to claim 16 wherein the polymerizable vinyl compounds comprise a solution of a polymeric, polymerizable vinyl compound selected from acrylated and methacrylated polyesters, acrylated and methacrylated polyethers, acrylated and methacrylated epoxy polymers, acrylated or methacrylated urethanes, and mixtures thereof, in a diluent selected from monomeric acrylate and methacrylate esters.

18. A polymeric coating composition according to claim 15 comprising a polymer of one or more acrylic acid esters, one or more methacrylic acid esters and/or other copolymerizable vinyl compounds, having copolymerized therein one or more of the colorant compounds having the formula:

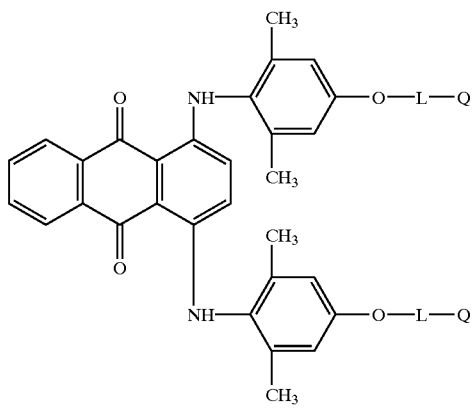

wherein L is —CH$_2$CH$_2$— or —CH$_2$CH(CH$_3$)—; and Q is a photopolymerizable group selected from the radicals having the formulae

—COC(R$_3$)=CH—R$_4$,  1

—CONHCOC(R$_3$)=CH—R$_4$,  2

—CONH—C$_1$–C$_6$-alkylene OCOC(R$_3$)=CH—R$_4$,  3

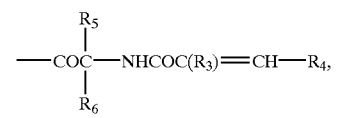  4

—COCH=CH—CO$_2$R$_7$,  5

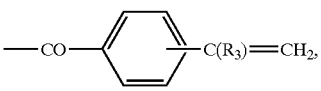  6

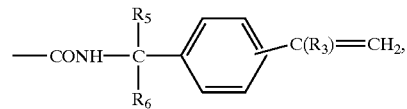  7

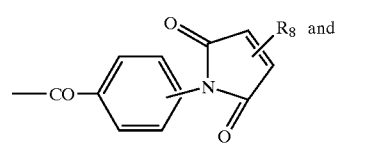  8

—COCH$_2$ĊCO$_2$R$_7$ and/or  —COCCH$_2$ĊO$_2$R$_7$  9 wherein
  $R_3$ is selected from hydrogen or $C_1$–$C_6$-alkyl;
  $R_4$ is selected from hydrogen; $C_1$–$C_6$-alkyl; phenyl; phenyl substituted with one or more groups selected from $C_1$–$C_6$-alkyl, $C_1$–$C_6$-alkoxy, —N($C_1$–$C_6$-alkyl)$_2$, nitro, cyano, $C_2$–$C_6$-alkoxycarbonyl, $C_2$–$C_6$-alkanoyloxy and halogen; 1- and 2-naphthyl; 1- and 2-naphthyl substituted with $C_1$–$C_6$-alkyl or $C_1$–$C_6$-alkoxy; 2- and 3-thienyl; 2- and 3-thienyl substituted with $C_1$–$C_6$-alkyl or halogen; 2- and 3-furyl; and 2- and 3-furyl substituted with $C_{1-6}$-alkyl;
  $R_5$ and $R_6$ are independently selected from hydrogen, $C_1$–$C_6$-alkyl, aryl, or $R_5$ and $R_6$ may be combined to represent a —(—CH$_2$—)$_{3-5}$— radical;
  $R_7$ is selected from hydrogen or a group selected from $C_1$–$C_6$-alkyl, $C_3$–$C_8$-alkenyl, $C_3$–$C_8$-cycloalkyl and aryl; and
  $R_8$ is selected from hydrogen, $C_1$–$C_6$ alkyl and aryl.

19. A polymeric composition according to claim 18 comprising a coating of an acrylic polymer of one or more acrylic acid esters, one or more methacrylic acid esters or a mixture thereof having copolymerized therein one or more of the colorant compounds defined in claim 18.

20. A polymeric composition according to claim 18 comprising a coating of an unsaturated polyester containing one or more maleate/fumarate residues; one or more monomers which contain one or more vinyl ether groups, one or more vinyl ester groups, or a combination thereof, and, optionally, one or more acrylic or methacrylic acid esters; or a mixture thereof having copolymerized therein one or more of the colorant compounds defined in claim 18.

21. A polymeric coating according to claim 19 containing from about 0.05 to 15.0 weight percent of the residue of one or more of the colorant compounds of claim 18 based on the weight of the coating.

* * * * *